(12) United States Patent
Minami et al.

(10) Patent No.: US 8,179,428 B2
(45) Date of Patent: May 15, 2012

(54) IMAGING APPARATUS FOR ELECTRONIC ENDOSCOPE AND ELECTRONIC ENDOSCOPE

(75) Inventors: Itsuji Minami, Saitama (JP); Kazuaki Takahashi, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1362 days.

(21) Appl. No.: 11/283,799

(22) Filed: Nov. 22, 2005

(65) Prior Publication Data

US 2006/0132598 A1    Jun. 22, 2006

(30) Foreign Application Priority Data

Nov. 24, 2004 (JP) .................................. 2004-339474
Nov. 24, 2004 (JP) .................................. 2004-339475

(51) Int. Cl.
*A61B 1/005* (2006.01)

(52) U.S. Cl. .............. 348/76; 348/45; 348/65; 600/101; 600/110; 600/130

(58) Field of Classification Search .................... 348/45, 348/65, 76; 600/130, 110, 101
See application file for complete search history.

(56) References Cited

U.S. PATENT DOCUMENTS

| | | | | |
|---|---|---|---|---|
| 4,809,680 A | * | 3/1989 | Yabe ............................... | 600/130 |
| 4,832,003 A | * | 5/1989 | Yabe ............................... | 600/109 |
| 4,866,516 A | * | 9/1989 | Hibino et al. ................... | 348/68 |
| 5,365,268 A | | 11/1994 | Minami et al. | |
| 6,040,612 A | | 3/2000 | Minami et al. | |

FOREIGN PATENT DOCUMENTS

| | | |
|---|---|---|
| EP | 0 566 861 A1 | 10/1993 |
| JP | 63-177106 A | 7/1988 |
| JP | 2853939 B2 | 11/1998 |
| JP | 2001-128937 A | 5/2001 |
| JP | 3186965 B2 | 5/2001 |
| JP | 3364574 B2 | 10/2002 |
| JP | 2003-259230 A | 9/2003 |

OTHER PUBLICATIONS

Japanese Office Action drafted Dec. 18, 2009, in corresponding Japanese Application No. 2004-339474.

* cited by examiner

*Primary Examiner* — King Poon
*Assistant Examiner* — Jamares Q Washington
(74) *Attorney, Agent, or Firm* — Birch, Stewart, Kolasch & Birch, LLP

(57) ABSTRACT

An imaging apparatus for an electronic endoscope includes a bare chip of CCD, a circuit board with approximately the same thickness as the bare chip, and a conducting plate with no less than 1/4 width of the bare chip. The bare chip has terminals on the surface with an imaging surface. The terminals are arranged near the edge facing the rear end of an insertion section of the electronic endoscope. The circuit board has terminals on the surface near the edge facing the front end of the insertion section. These terminals are connected by wire bonding. The conducting plate is attached along one side of the rear surface of the CCD and the circuit board for electrical connection. A forceps channel is provided such that its outer circumference fits partially into a cut portion formed on the rear surfaces of the CCD and the circuit board by the conducting plate.

2 Claims, 4 Drawing Sheets

IMAGING APPARATUS FOR ELECTRONIC ENDOSCOPE AND ELECTRONIC ENDOSCOPE

BACKGROUND OF THE INVENTION

1. Field of the Invention

The present invention relates to an imaging apparatus for an electronic endoscope for imaging an object in a body cavity, and an electronic endoscope having the imaging apparatus built-in.

2. Description of the Related Arts

Medical diagnoses using an electronic endoscope are widely performed. An imaging apparatus with an imaging device such as a CCD is built in a front end of an insertion section of the electronic endoscope, which is inserted into a body cavity. A processor device applies signal processing to an imaging signal obtained with the CCD, and an image in the body cavity can be observed on a monitor. Since a forceps channel through which a treatment tool is inserted is provided in the insertion section, biopsy in which affected tissue is removed with the treatment tool can be performed with observing the image in the body cavity.

As the imaging apparatus for the electronic endoscope, there is a type that uses a prism for guiding image light transmitted through an objective optical system to an imaging surface. In this type, the objective optical system for taking in the image light of the object in the body cavity is positioned at the front end of the insertion section of the electronic endoscope, and the CCD is arranged such that the imaging surface is parallel to an optical axis of the objective optical system. In regard to this type of imaging apparatus, dimension (thickness) in a direction vertical to the optical axis of the entire imaging apparatus including the objective optical system, the CCD, and the prism directly influences a diameter of the front end of the insertion section of the electronic endoscope. Therefore, various attempts have been made to narrow the diameter of the insertion section of the electronic endoscope by reducing the thickness of the entire imaging apparatus as possible (see Japanese Patents No. 2853939, 3364574, and 3186965).

The Patent No. 2853939 discloses a CCD package constituted of a bottom board and a reinforcement board. The bottom board includes an extended portion in a predetermined direction, and a CCD is placed on the surface thereof. The reinforcement board includes a containing hole to be placed on the surface of the bottom-base plate to form a containing portion of the CCD and an extended portion in a predetermined direction. The thickness of the bottom base plate is less than 0.5 mm. The extended portions of both the boards are overlapped to form the extended portion extending in one direction from one side of the boards. Terminals are provided on the extended portion. According to the CCD package, since the connecting pins protruding toward the bottom of a conventional package are not required, the signal lines can be wired by using an upper space of the extended portion, so that it is possible to reduce the entire thickness of the CCD package.

The Patent No. 3364574 discloses an imaging apparatus for the electronic endoscope in which the CCD package is not required. A conductor lead is formed by a TAB (Tape Automated Bonding) method in a terminal of the CCD so as to protrude from its outer circumference, and the CCD is provided in an opening hole of a circuit board to connect the conductor lead to a terminal of the circuit board.

The Patent No. 3186965 discloses a camera head device for the electronic endoscope. In the camera head device, an empty area where the terminals are not arranged is provided among the connecting terminal array on the CCD, and a supporting member of the objective optical system is attached to the empty area. According to the camera head device, since it is unnecessary to arrange the supporting member so as to avoid the bonding wires used for connecting the terminals, so that the diameter of the electronic endoscope can be narrow.

In the Japanese Patent Laid-Open Publication No. 2001-128937, the diameter of the insertion section is narrowed by devising the arrangement of the components in the insertion section. Signal cables, which are formed by bundling plural signal lines extending from an imaging device, are divided, and the signal cable having the largest outside diameter is closely arranged in a gap having the largest inside diameter of all gaps, which are formed between outer circumference of the incorporated object (forceps channel) having the largest outer circumference of all the incorporated objects and inner circumference of the insertion section. The outside diameters of the signal cable having the largest outside diameter and other signal cables are determined such that the inside diameter of the gap is the smallest at the time when these signal cables are arranged in the gap.

However, since the CCD is placed on the board in the Patent Nos. 2853939 and 3186965, the entire thickness becomes large. In addition, in the Patent No. 2853939, the plural boards having a special shape have to be used, and in the Patent No. 3186965, the layout of the terminals should be considered to provide the empty area. Therefore, there is a problem that the part cost is increased in both the cases.

In the Patent No. 3364574, since the CCD package is not required, the entire thickness is reduced in comparison with the above two cases. However, since the opening hole for arranging the CCD on the circuit board is required, there is also a problem that the part cost is increased.

In the Japanese Patent Laid-Open Publication No. 2001-128937, although the diameter of the insertion section is narrowed by dividing the signal cables, since the imaging device and the forceps channel which occupy the most of the area in the insertion section are not considered, the problem is not solved fundamentally.

SUMMARY OF THE INVENTION

An object of the present invention is to narrow a diameter of an insertion section of an electronic endoscope.

In order to achieve the above object, an imaging apparatus for an electronic endoscope of the present invention is provided with an imaging device constituted of a bare chip and a circuit board attached to the bare chip. Signal terminals are provided on a surface having an imaging surface and arranged near the edge portion facing a rear end side of an insertion section of the electronic endoscope. The circuit board has approximately the same thickness as the bare chip, and the signal terminals to be connected to signal terminals of the bare chip by wire bonding are arranged near the edge portion facing a front end side of the insertion section.

In a preferable embodiment of the present invention, a conducting plate is provided in the imaging apparatus for the electronic endoscope. The conducting plate is attached to a rear surface of the bare chip and a rear surface of the circuit board, and connects the bare chip to the circuit board electrically. The conducting plate has a width no less than ¼ width of the bare chip, and it is arranged along one side of the rear surfaces of the bare chip and circuit board. A drive control signal of an electronic shutter is input to the imaging device through the conducting plate.

An electronic endoscope of the present invention is provided with an imaging device constituted of a bare chip, a circuit board attached to the bare chip, an imaging device having a conducting plate attached to a rear surface of the bare chip and a rear surface of the circuit board for connecting the bare chip to the circuit board electrically, and a forceps channel for inserting a treatment tool into a body cavity. Signal terminals are concentrated and arranged near the edge portion facing a rear end side of an insertion section of the electronic endoscope on a surface having an imaging surface. The circuit board has approximately the same thickness as the bare chip, and the signal terminals to be connected to signal terminals of the bare chip by wire bonding are arranged near the edge facing the front end of the insertion section. The conducting plate has a width of no less than ¼ width of the bare chip, and it is arranged along one side of the rear surfaces of the bare chip and circuit board. The forceps channel is arranged such that apart of the outer circumference fits into a cut portion, which is formed in the rear surfaces of the bare chip and the circuit board by the conducting plate.

The imaging apparatus for the electronic endoscope of the present invention uses the bare chip for the imaging device, and the circuit board having approximately the same thickness as the bare chip is attached to the imaging device. The bare chip and the circuit board are connected electrically to each other through the signal terminals, which are arranged near the edges on their surface, so that the thickness from the imaging device to the cover glass can be reduced extremely. Thereby, the diameter of the insertion section of the electronic endoscope can be narrowed. In addition, the imaging apparatus for the electronic endoscope is constituted of parts without requiring complicate processing, so that it can be produced at low cost.

Moreover, since the conducting plate is bridged over the rear surfaces of the imaging device and the circuit board, the adhesive attachment of the imaging device to the circuit board is mechanically enhanced. Further, driving heat of the imaging device can be dissipated efficiently.

According to the electronic endoscope of the present invention, since the forceps channel is arranged such that the outer circumference fits into the cut portion, which is formed in the rear surfaces of the imaging device and the circuit board by the conducting plate, it is possible to reduce the dimension in a direction that the imaging apparatus and the forceps channel are lined, so that the insertion section of the electronic endoscope can be narrowed moreover.

BRIEF DESCRIPTION OF THE DRAWINGS

The above and other subjects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein.

DETAILED DESCRIPTION OF THE PREFERRED EMBODIMENTS

Figure 1:
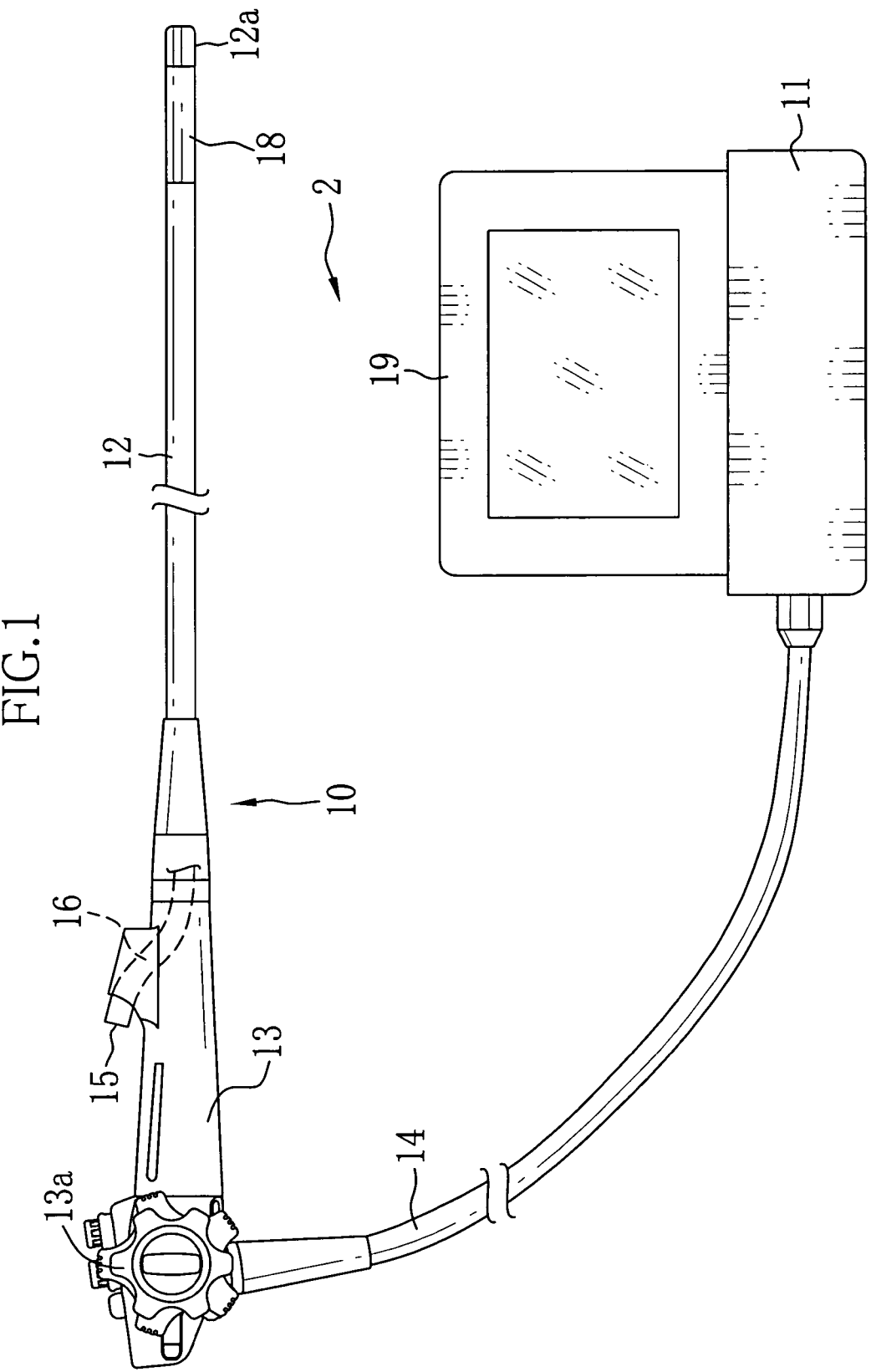
FIG. 1 is a schematic view showing a structure of an electronic endoscope device.

In FIG. 1, an electronic endoscope apparatus 2 is constituted of an electronic endoscope 10, a processor device 11, a light source device (not shown) and so forth. The electronic endoscope 10 is provided with an insertion section 12 to be inserted into a body cavity, an operating section 13 connected to a base end portion of the insertion section 12, and a cord 14 for the connection to the processor device 11 and the light source device. The operating section 13 is provided with a forceps opening 15 into which a treatment tool is inserted. The forceps opening 15 is connected to a forceps channel 16 provided in the insertion section 12 as shown by dashed lines. An imaging apparatus 17 (see FIG. 2) for imaging the inside of the body cavity is built in a front end portion 12a provided over the front end of the insertion section 12.

A curving portion 18 to which plural curving pieces are connected is provided behind the front end portion 12a. A wire provided in the insertion section 12 is pushed and pulled by operating an angle knob 13a provided in the operating section 13 to curve and move the curving portion 18 in the up, down, left and right directions, so that the front end portion 12a can be directed in any direction inside the body cavity.

A signal processor for applying various kinds of signal processing to image signals obtained with the imaging apparatus 17 is mounted in the processor device 11. Meanwhile, a light source for supplying an illumination light to the electronic endoscope 10 through the cord 14 is mounted in the light source device. The image in the body cavity taken by the imaging apparatus 17 can be observed on a monitor 19.

Figure 2:
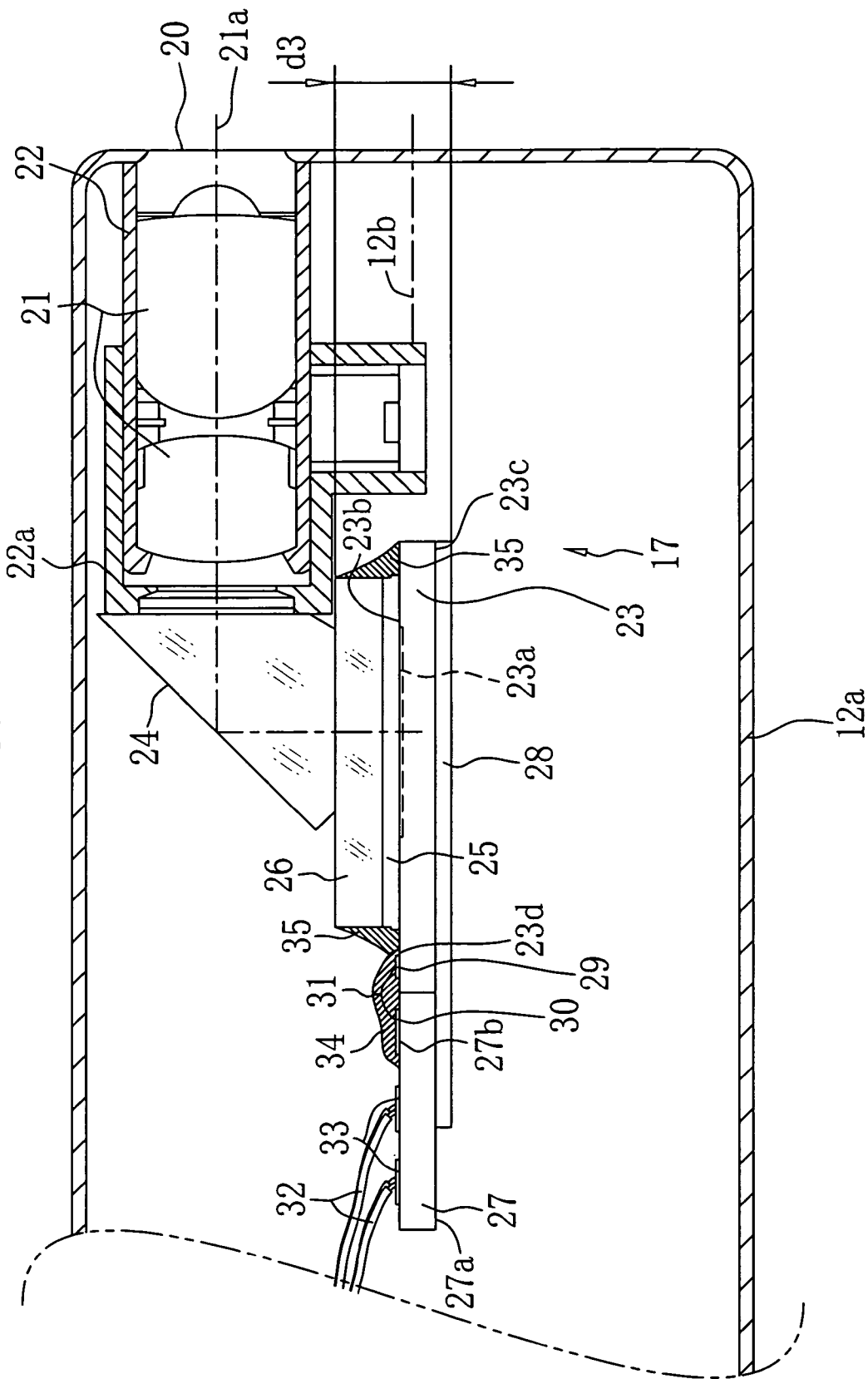
FIG. 2 is an enlarged partial cross-sectional view showing a structure of a front end of an insertion section of the electronic endoscope.

In FIG. 2, an observing window 20 is provided in the front end portion 12a. The observing window 20 is provided with a lens barrel 22 holding an objective optical system (lens group) 21 for taking in an image light of an observed site in the body cavity. The lens barrel 22 is attached such that an optical axis 21a of the objective optical system 21 is parallel to a central axis 12b of the insertion section 12.

A prism 24 for guiding the image light of the observed site passed through the objective optical system 21 to a CCD 23 is connected to a rear end of the lens barrel 22 through a lens barrel supporting frame 22a. The prism 24 is connected to a cover glass 26. Thereby, the optical axis 21a of the objective optical system 21 and an imaging surface 23a of the CCD 23 becomes parallel to each other. Note that an illumination window, a forceps outlet (not shown), and the like are provided in the front end portion 12a. The illumination window emits the illumination light from the light source device to the observed site in the body cavity, and the forceps outlet connects with the forceps opening 15 through the forceps channel 16.

Figure 3:
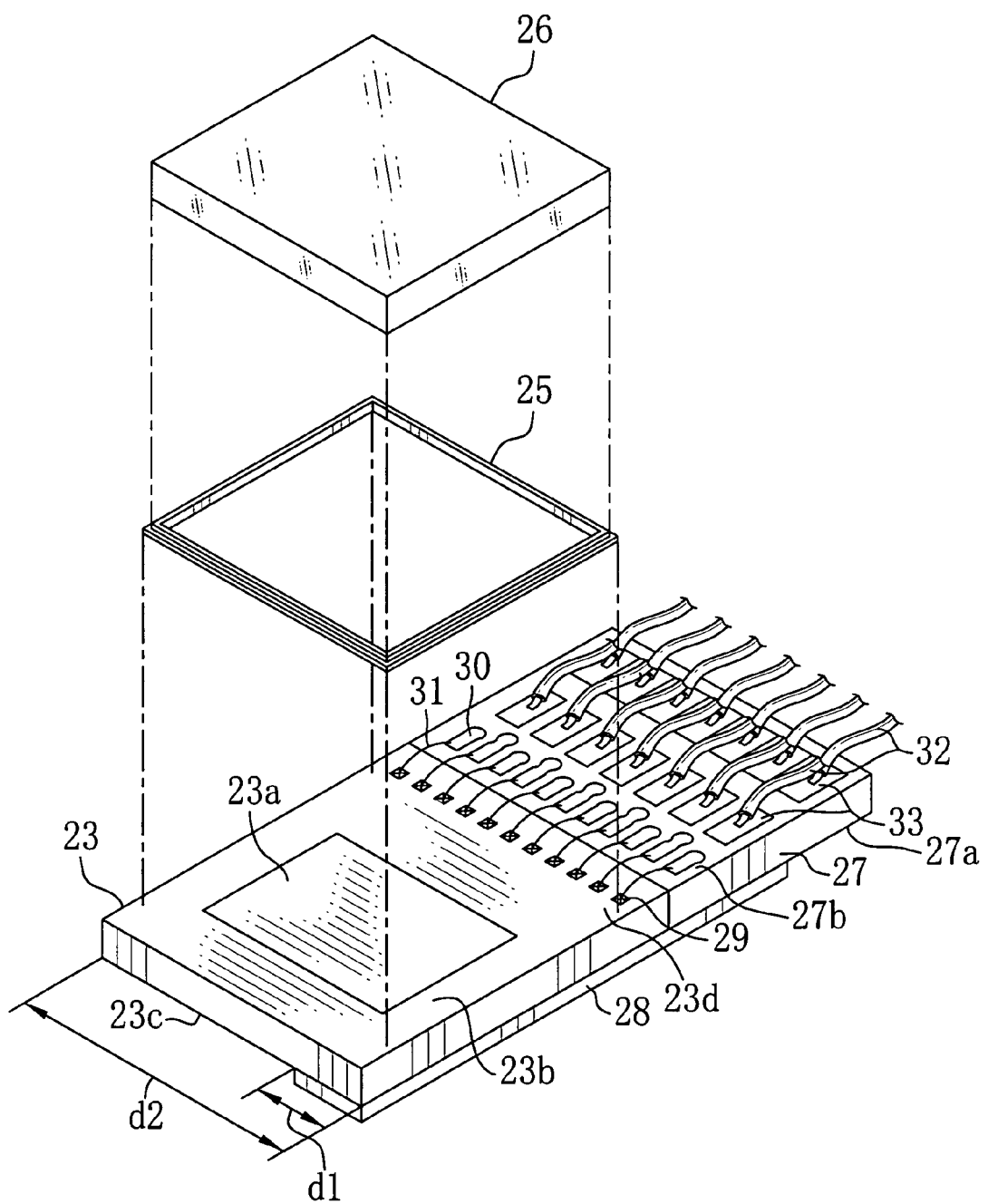
FIG. 3 is an exploded perspective view showing structures of a CCD, a spacer, a cover glass, and a circuit board.

The CCD 23 is constituted of an inter line type of CCD, for example, and a bare chip in which the imaging surface 23a is provided on a surface 23b. As shown in FIG. 3, the cover glass 26 having a rectangular shape is attached onto the imaging surface 23a through a spacer 25 having a square frame shape. The CCD 23, the spacer 25 and the cover glass 26 are adhered to each other with an adhesive agent.

A circuit board 27 having approximately the same thickness as the CCD 23 is adhered to a rear end surface of the CCD 23 with an adhesive agent. A conducting plate 28 is attached to a rear surface 23c of the CCD 23 and a rear surface 27a of the circuit board 27 with silver paste. The conducting plate 28 connects the CCD 23 to the circuit board 27 electrically through a through hole (not shown). A drive control signal for an electronic shutter, for example an overflow drain control signal is input to the CCD 23 through the conducting plate 28.

In order to reinforce the adhesive attachment of the CCD 23 to the circuit board 27 mechanically, a width d1 of the conducting plate 28 is no less than ¼ of a width d2 of the CCD 23. The conducting plate 28 is made from the material excellent in a heat radiation property such as a copper plate. Note that the conducting plate 28 is formed to have the thickness of about 0.2 mm.

All terminals 29 are provided on the surface 23*b* and arranged in a portion 23*d* near the edge facing a rear end side of the insertion section 12. Meanwhile, all terminals 30 are arranged in a portion 27*b* near the edge facing a front end side of the insertion section 12 to correspond to the portion 23*d*. The terminals 29, 30 are connected electrically to each other through bonding wires 31. Input-output terminals 33 are provided in the rear end side of the terminal 30 on the circuit board 27. Signal lines 32 for inputting and outputting various signals to/from the processor device 11 through the cord 14 are soldered on the input-output terminals 33.

The terminals 29, 30 and the bonding wire 31 are sealed with a sealing agent 34. In order to ensure airtightness of a gap between the CCD 23 and the cover glass 26 formed by the spacer 25, a sealing agent 35 is applied so as to cover side edges of the spacer 25 and the cover glass 26. The sealing agents 34, 35 are made from a one-part curable epoxy resin, for example.

The sealing agent 35 is applied after the CCD 23 attached to the cover glass 26 through the spacer 25 is adhered to the circuit board 27, and the terminals 29, 30 are connected to each other with the bonding wires 31, and then these terminals and the bonding wires 31 are sealed with the sealing agent 34.

Figure 4:
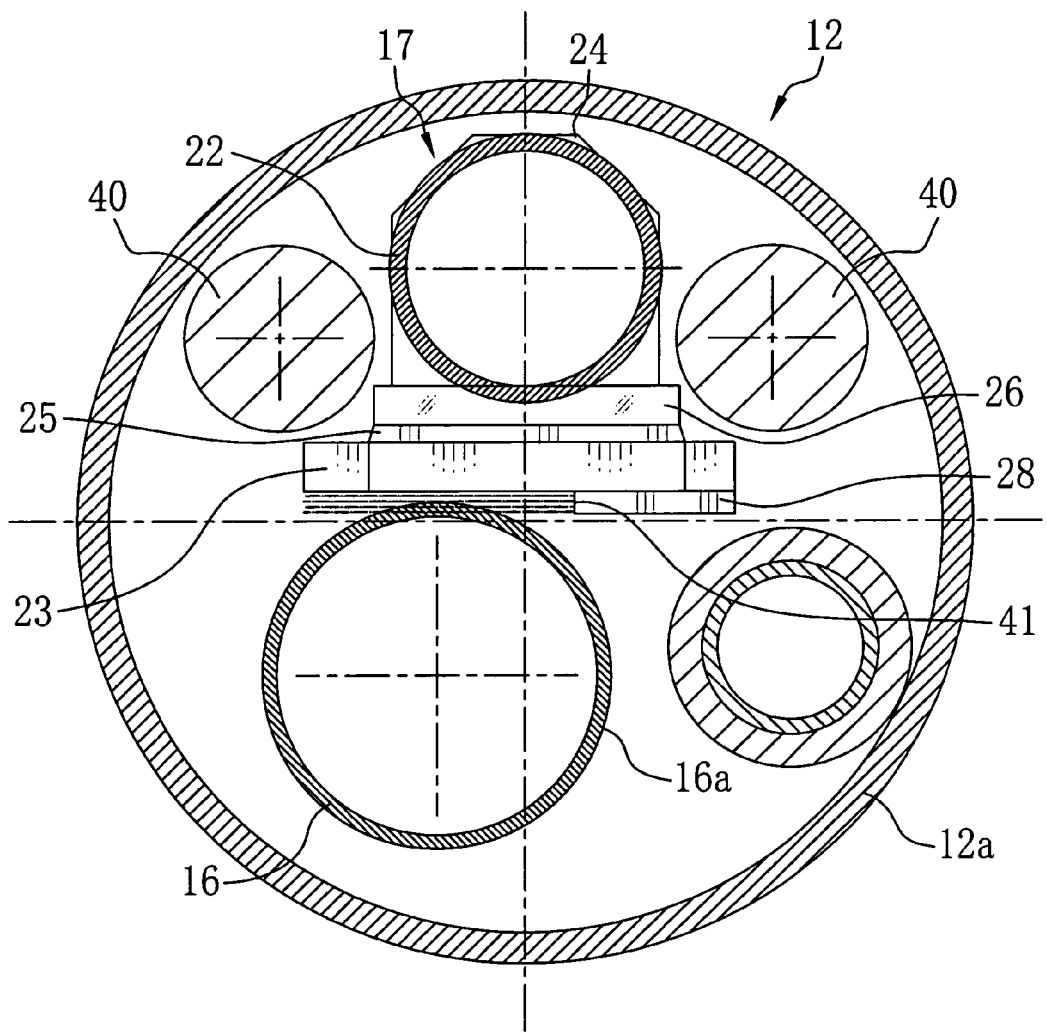
FIG. 4 is a cross-sectional view of the front end of the insertion section.

As shown in FIG. 4, in addition to the imaging apparatus 17, a pair of optical fibers 40 as a light guide are provided in the front end portion 12*a*. The optical fibers 40 are arranged in both sides of the forceps channel 16 and the imaging apparatus 17, and guide the illumination light to the illumination window. The forceps channel 16 is provided such that a part of an outer circumference 16*a* fits into a cut portion 41 (an area shown by dashed lines), which is formed on the rear surfaces 23*c*, 27*a* of the CCD 23 and the circuit board 27 by the conducting plate 28.

When the imaging apparatus 17 is produced, the cover glass 26 is attached on the imaging surface 23*a* of the CCD 23 through the spacer 25. After the attachment of the cover glass 26, the circuit board 27 is adhered to the rear end surface of the CCD 23. Subsequently, the terminals 29, 30 are connected with each other by the bonding wires 31. The terminals 29, 30 and the bonding wires 31 are sealed by the sealing agent 34. Then, the sealing agent 35 is applied so as to cover the side edges of the spacer 25 and the cover glass 26.

After the application of the sealing agent 35, the conducting plate 28 is positioned along one side of the rear surfaces of the CCD 23 and the circuit board 27, and bridges over them. At this time, the CCD 23 and the circuit board 27 are electrically connected to each other by the conducting plate 28 through a through hole provided in the CCD 23 and the circuit board 27. Finally, the cover glass 26 is attached with the adhesive agent to the prism 24 connected to the lens barrel supporting frame 22*a*.

The imaging apparatus 17 produced by the above process is built in the front end portion 12*a*, and the forceps channel 16 is arranged such that the part of the outer circumference 16*a* is inserted into the cut portion 41, so that the electronic endoscope 10 is completed.

In endoscopic diagnosis, after the electronic endoscope 10 is connected to the light source device and the processor device 11 through the cord 14, the insertion section 12 is inserted into the body cavity, and then the image of the observed site in the body cavity taken by the imaging apparatus 17 is observed on the monitor 19.

In the above embodiment, the imaging apparatus 17 having the CCD 23 and the circuit board 27 is used. In the CCD 23, all the terminals 29 are arranged in the marginal portion 23*d* of the rear end side of the insertion section 12 on the surface 23*b* having the imaging surface 23*a*. The circuit board 27 having approximately the same thickness as the CCD 23 is attached to the CCD 23, and in the circuit board 27, all the terminals 30 to be connected to the terminals 29 by the wire bonding are arranged in the near edge portion 27*b* of the front end side of the insertion section 12. Therefore, as shown in FIG. 2, thickness d3 from the CCD 23 to the cover glass 26 can be reduced extremely.

In addition, the thickness of the imaging apparatus 17 is composed only of the thickness of the CCD 23 as the bare chip, the cover glass 26, and the conducting plate 28, and there is no need to count the thickness of the base plate and the package. In addition, the imaging apparatus 17 can be produced from the parts which can be formed by simple processes, eliminating the need of producing a base plate with special shape.

Moreover, since the conducting plate 28 is bridged over the rear surfaces 23*c*, 27*a* of the CCD 23 and the circuit board 27, the adhesive attachment of the CCD 23 to the circuit board 27 is mechanically enhanced, and in addition, the heat generated in the CCD 23 and the circuit board 27 in driving the CCD 23 is dissipated efficiently through the conducting plate 28.

Furthermore, the forceps channel 16 is arranged such that the part of the outer circumference 16*a* fits into the cut portion 41, which is formed on the rear surfaces 23*c*, 27*a* of the CCD 23 and the circuit board 27 by the conducting plate 28, so that it is possible to reduce the dimension in the direction that the imaging apparatus 17 and the forceps channel 16 are lined. Accordingly, the diameter of the insertion section 12 can be narrowed moreover.

The width d1 of the conducting plate 28 needs only to be no less than ¼ of the width d2 of the CCD 23, and it may have approximately the same with as d2.

In the above embodiment, although the spacer 25 is used to form the gap between the CCD 23 and the cover glass 26, a transparent adhesive agent may be used instead of the spacer 25, or legs may be formed in the cover glass 26.

Moreover, the above embodiment uses a so-called direct-view type of the electronic endoscope 10 and the optical axis 21*a* of the objective optical system 21 is set parallel to the central axis 12*b* of the insertion section 12. However, the present invention is applicable to a lateral-view type of electronic endoscope as long as the optical axis 21*a* and the imaging surface 23*a* of the CCD 23 are set parallel to each other.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope insertable into a body cavity, comprising:

an imaging device arranged in a front end of an insertion section of said electronic endoscope for imaging an inside of said body cavity, wherein said imaging device comprises:

an objective optical system for taking in image light reflected by an object in said body cavity;

an imaging device arranged such that an imaging surface becomes parallel to an optical axis of said objective optical system, said imaging device being constituted of a bare chip and first signal terminals, said first signal terminals being provided on a surface having said imaging surface, and arranged near an edge portion facing a rear end of said insertion section;

a prism for guiding said image light to said imaging surface;

a cover glass attached onto said imaging surface to form a gap between said image surface and said prism;

a circuit board attached to said bare chip, said circuit board having approximately a same thickness as said bare chip, second signal terminals connected to said first signal terminals by wire bonding and being arranged near an edge portion facing a front end side of said insertion section;

a conducting plate having a width which is smaller than a width of said bare chip, wherein one edge of said conducting plate is aligned with one lateral edge of said rear surfaces of said bare chip and said circuit board, said one edge of said conducting plate and said one edge of said rear surfaces extending in parallel to said optical axis of said objective optical system, and said conducting plate electrically connects said bare chip and said circuit board to each other;

a cut portion formed by an edge face of said conducting plate and by said rear surfaces of said bare chip and said circuit board, said edge face extending in parallel to said optical axis of said objective lens system; and a forceps channel for inserting a treatment tool into said body cavity, wherein said forceps channel is arranged such that a part of an outer circumference of said forceps channel fits into said cut portion, said outer circumference of said forceps channel having a constant diameter in a direction of said optical axis.

2. The electronic endoscope as claimed in claim 1, wherein said imaging device inputs a drive control signal for an electronic shutter through said conducting plate.

* * * * *